United States Patent
Mitidieri et al.

(10) Patent No.: US 11,969,403 B2
(45) Date of Patent: Apr. 30, 2024

(54) TOPICAL FORMULATIONS OF CHLOROPROCAINE AND METHODS OF USING SAME

(71) Applicant: Sintetica S.A., Mendrisio (CH)

(72) Inventors: Augusto Mitidieri, Lugano (CH); Elisabetta Donati, Mendrisio (CH); Clara Bianchi, Torno (IT)

(73) Assignee: Sintetica S.A., Mendrisio (CH)

( * ) Notice: Subject to any disclaimer, the term of this patent is extended or adjusted under 35 U.S.C. 154(b) by 242 days.

(21) Appl. No.: 17/008,913

(22) Filed: Sep. 1, 2020

(65) Prior Publication Data

US 2020/0390738 A1 Dec. 17, 2020

Related U.S. Application Data

(62) Division of application No. 16/131,174, filed on Sep. 14, 2018, now Pat. No. 10,792,271.

(60) Provisional application No. 62/559,220, filed on Sep. 15, 2017.

(51) Int. Cl.

| | |
|---|---|
| *A61K 31/245* | (2006.01) |
| *A61K 9/00* | (2006.01) |
| *A61K 9/06* | (2006.01) |
| *A61K 47/02* | (2006.01) |
| *A61K 47/12* | (2006.01) |
| *A61K 47/38* | (2006.01) |
| *A61P 23/02* | (2006.01) |

(52) U.S. Cl.
CPC .......... *A61K 31/245* (2013.01); *A61K 9/0048* (2013.01); *A61K 9/06* (2013.01); *A61K 47/02* (2013.01); *A61K 47/12* (2013.01); *A61K 47/38* (2013.01); *A61P 23/02* (2018.01)

(58) Field of Classification Search
CPC ...... A61K 31/245; A61K 47/02; A61K 47/12; A61K 47/38; A61K 9/0048; A61K 9/06; A61P 23/02
See application file for complete search history.

(56) References Cited

U.S. PATENT DOCUMENTS

| | | |
|---|---|---|
| 6,218,428 B1 | 4/2001 | Chynn |
| 8,969,412 B2 | 3/2015 | Mitidieri et al. |
| 2005/0137177 A1 | 6/2005 | Shafer |

FOREIGN PATENT DOCUMENTS

| | | |
|---|---|---|
| JP | 2004123634 A | 4/2004 |
| WO | 2004058329 A2 | 7/2004 |

OTHER PUBLICATIONS

Akten, Highlights of Prescribing Information, NDA 22221/S-005, p. 3-6, Sep. 2013.
Kumar, Degree of Ionization, Degree of Ionization—an overview | ScienceDirect Topics, 15 pp, Apr. 10, 2020.
Hammer et al., Short Acting Soft Mydriatics, Current Eye Research, ISSN: 0271-3683 (Print) 1460-2202 (Online) Journal homepage: https://www.tandfonline.com/loi/icey20.
Leopold et al., Percutaneous Penetration of Local Anesthetic Bases: Pharmacodynamic Measurements, Department of Dermatology, School of Medicine, University of California, San Francisco, California, U.S.A., The Society for Investigative Dermatology, Inc.; 113:304-307, 1999.
Farzi et al.; Addition of Intrathecal Fentanyl or Meperidine to Lidocaine and Epinephrine for Spinal Anesthesia in Elective Cesarean Delivery, Anesth Pain Med. Feb. 2014; 4(1): e14081, 7 pp.
Liu et al.; Ocular and systemic pharmacokinetics of lidocaine hydrochloride ophthalmic gel in rabbits after topical ocular administration, Eur J Drug Metab Pharmacokinet (2015) 40:409-415, 7 pp.
Mclure et al.; Review of local anaesthetic agents, Minerva Anestesiologica 2005;71:59-74.
Natrosol Product Information, Formulating elegant liquid and semi-solid drug products, Ashland, 2018 32 pp.
Manassero et al.; Prilocaine hydrochloride 2% hyperbaric solution for intrathecal injection: a clinical review, Dove Press Journal: Local and Regional Anesthesia, Mar. 31, 2017, 10 pp.
Shah et al.; New local anesthetics, Elsevier, Best Practice & Research Clinical Anaesthesiology 32 (2018) 179-185.
Liu et al.; Topical bupivacaine and proparacaine: a comparison of toxicity, onset of action, and duration of action, abstract, PubMed, NCBI, Aug. 11, 2019, 2 pp.
Mcgee et al.; Toxicities of topical ophthalmic anesthetics, ISSN: 1474-0338 (Print) 1744-764X (Online) Journal homepage: https://www.tandfonline.com/loi/ieds20, Oct. 30, 2007, 5 pp.
Tropicamide Ophthalmic Solution, USP, package insert, Bausch & Lomb Incorporated, 2019, 2 pp.
Declaration of Laurence Feraillee, PH.D, filed in U.S. Appl. No. 16/131,174, United States Patent and Trademark Office, Mar. 5, 2020, 6 pp.
Sintetica S.A .; PCT/IB2018/057073; International Search Report and Written Opinion; ISA/EP; dated Nov. 13, 2018; 14 pages.
Cass, et al.; Randomized double-blind study of the clinical duration and efficacy of Nesacaine-MPF 2% and 3% in peribulbar anesthesia; Journal Cataract and Refractive Surgery, vol. 25, No. 12; Dec. 1, 1999; 6 pages.
US FDA Prescribing Information for Nesacaine-chloroprocaine hydrochloride injection, solution General Injectables & Vaccines, Inc (Jul. 2010), 12 pages.
Garcia-Valldecabres et al.; Optometry, vol. 75, No. 3, Mar. 2004, pp. 161-168 (Year: 2004).
Reichert et al., Techniques in Regional Anesthesia and Pain Management, vol. 8, No. 3, pp. 106-109 (Year: 2004).

*Primary Examiner* — Kara R Mcmillian
(74) *Attorney, Agent, or Firm* — Clark G. Sullivan

(57) ABSTRACT

Topical dosages and formulations of chloroprocaine and pharmaceutically acceptable salts thereof are provided that are efficacious, chemically stable and physiologically balanced for safety and efficacy, particularly during ophthalmic procedures or in response to ophthalmic abrasions or trauma.

9 Claims, No Drawings

TOPICAL FORMULATIONS OF CHLOROPROCAINE AND METHODS OF USING SAME

FIELD OF INVENTION

The present invention relates to topical dosage forms and formulations of chloroprocaine for inducing local anesthesia and analgesia, that are therapeutically effective, chemically stable, and particularly useful for short ophthalmic medical procedures

BACKGROUND OF INVENTION

Topical anesthetics are marketed without prescription for the relief of various conditions including sunburn, minor burns, insect bites and stings, poison ivy, poison oak, poison sumac, and minor cuts and abrasions. They are also used during minor surgical procedures. Dentists use them to numb oral tissue before injecting a local anesthetic; ophthalmologists use them to numb the surface of the eye when performing minor surgeries and medical procedures; and otolaryngologists use them when performing procedures in the ear canal. Molecules approved as topical anesthetics in the United States and Europe include lidocaine, benzocaine, prilocaine, and oxybuprocaine, among others.

Chloroprocaine HCl is a short acting spinal anesthetic that is available in Europe and the United States in injectable dosage forms. It approved in Europe for surgical procedures up to 40 minutes, and in the United States for intrathecal use and for the production of local anesthesia by infiltration and peripheral nerve block. An intrathecal injectable formulation is reported in U.S. Pat. No. 8,969,412 to Sintetica S.A. This formulation comprises chloroprocaine HCl, sodium chloride, and enough hydrochloric acid to impart a pH of from 3 to 4. The patent also reports that it is important when manufacturing chloroprocaine dosage forms to work in an oxygen free environment purged with nitrogen, to prevent degradation of the chloroprocaine. Other injectable formulations of chloroprocaine are reported in the FDA-approved prescribing information for Nesacaine®. These formulations contain chloroprocaine HCl (1-3%), sodium chloride, and optionally disodium EDTA dehydrate and methylparaben. The molecule has never been approved in a topical formulation, presumably because it is highly hydrophilic and does not pass through the skin.

Despite these existing treatments, there remains a need for topical anesthetics, particularly for formulations that are clear and sterile and suitable for use in ophthalmic procedures. These formulations should be characterized by:
  a consistent anesthetic effect with no significant patient to patient variability;
  predictable duration of anesthetic effect; and
  a short duration of action particularly for use in short medical procedures.
Chloroprocaine HCl has never been manufactured in a topical dosage form and could be attractive, particularly if the stability and manufacturing issues with the molecule could be overcome.

SUMMARY OF THE INVENTION

After extensive research and experimentation, the inventors have developed topical formulations and dosage forms of chloroprocaine with a well-defined anesthesia profile, that are both stable and clear, and particularly suitable for use in minor ophthalmic surgeries and procedures. Thus, in a first principal embodiment the invention provides a topical formulation for inducing local analgesia or anesthesia comprising: (a) a therapeutically effective amount of chloroprocaine or a pharmaceutically acceptable salt thereof for inducing said local analgesia or anesthesia; (b) one or more thickening agents; and (c) water.

A particularly suitable thickening agent is hydroxyethyl cellulose which, it has been discovered, exerts a stabilizing influence on the chloroprocaine. Whereas chloroprocaine must normally be handled in an oxygen-free environment purged with an inert gas such as nitrogen to prevent degradation of the chloroprocaine, the inventors have discovered that chloroprocaine formulated with hydroxyethyl cellulose does not require purging with an inert gas.

Other embodiments derive partly from the consistent anesthetic effect and duration of action of the formulations, and medical uses enabled thereby. Thus, in still another embodiment the invention provides a method of inducing local analgesia or anesthesia in a mammalian subject in need thereof comprising topically administering to said mammal a formulation of the present invention.

Additional advantages of the invention are set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Definitions and Use of Terms

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

As used in the specification and claims, the singular forms a, an, and the include plural references unless the context clearly dictates otherwise. For example, the term "a pharmaceutical excipient" refers to one or more pharmaceutical excipients for use in the presently disclosed formulations and methods.

When used herein the term "about" will compensate for variability allowed for in the pharmaceutical industry and inherent in pharmaceutical products, such as differences in product strength due to manufacturing variation and time-induced product degradation. In one embodiment the term allows for any variation which in the practice of pharmaceuticals would allow the product being evaluated to be considered pharmaceutically equivalent or bioequivalent to the recited strength. In another embodiment the term allows for any variation within 5% of the recited strength or concentration of the formulation.

The terms "treating" and "treatment," when used herein, refer to the medical management of a patient with the intent to cure, ameliorate, stabilize, or prevent a disease, pathological condition, injury, or disorder (collectively "disorder"). This term includes active treatment, that is, treatment directed specifically toward the improvement of a disorder, and also includes causal treatment, that is, treatment directed toward removal of the cause of the associated disorder. In addition, this term includes palliative treatment, that is, treatment designed for the relief of symptoms rather than the curing of the disorder; preventative treatment, that is, treatment directed to minimizing or partially or completely inhibiting the development of the disorder; and supportive treatment, that is, treatment employed to supplement another specific therapy directed toward the improvement of the disorder.

As used herein, "therapeutically effective amount" refers to an amount sufficient to elicit the desired biological response. The therapeutically effective amount or dose will depend on the age, sex and weight of the patient, and the current medical condition of the patient. The skilled artisan will be able to determine appropriate dosages depending on these and other factors in addition to the present disclosure.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. "Pharmaceutically acceptable salts" means salts that are pharmaceutically acceptable, as defined above, and which possess the desired pharmacological activity.

When a weight of an active ingredient is given without reference to the free base or salt of the active ingredient, it will be understood that the weight can refer to the weight of the free base or the weight or the entire salt. In like manner, when the molecule can exist as a hydrate, and the weight of the molecule is given, it will be understood that the weight can be refer to the weight of the hydrate or the weight of the molecule without the waters of hydration.

When ranges are expressed herein by specifying alternative upper and lower limits of the range, it will be understood that the endpoints can be combined in any manner that is mathematically feasible. Thus, for example, a range of from 50 or 80 to 100 or 70 can alternatively be expressed as a series of ranges of from 50 to 100, from 50 to 70, and from 80 to 100. When a series of upper bounds and lower bounds are related using the phase and/or, it will be understood that the upper bounds can be unlimited by the lower bonds or combined with the lower bounds, and vice versa. Thus, for example, a range of greater than 40% and/or less than 80% includes ranges of greater than 40%, less than 80%, and greater than 40% but less than 80%.

When percentages, concentrations or other units of measure are given herein, it will be understood that the units of measure are weight percent unless otherwise stated to the contrary.

Discussion of Principal Embodiments

The invention can be defined based on several principal embodiments which can be combined in any manner physically and mathematically possible to create additional principal embodiments.

In a first principal embodiment the invention provides a topical formulation for inducing local analgesia or anesthesia comprising: (a) a therapeutically effective amount of chloroprocaine or a pharmaceutically acceptable salt thereof for inducing said local analgesia or anesthesia; (b) one or more thickening agents, preferably hydroxyethyl cellulose; and (c) water.

In a second principal embodiment the invention provides a topical gel for inducing local analgesia or anesthesia comprising: (a) a therapeutically effective amount of chloroprocaine or a pharmaceutically acceptable salt thereof for inducing said local analgesia or anesthesia; (b) one or more thickening agents, preferably hydroxyethyl cellulose; and (c) water.

In a third principal embodiment the invention provides an ophthalmic topical gel for inducing local analgesia or anesthesia comprising: (a) a therapeutically effective amount of chloroprocaine or a pharmaceutically acceptable salt thereof for inducing said local analgesia or anesthesia; (b) one or more thickening agents, preferably hydroxyethyl cellulose; and (c) water.

In a fourth principal embodiment the invention provides a method of manufacturing the formulation of the present invention comprising admixing chloroprocaine or a pharmaceutically acceptable salt thereof, one or more thickening agents, a pH adjuster, and water to make a formulation.

In a fifth principal embodiment the invention provides a method of inducing local analgesia or anesthesia in a mammalian subject in need thereof comprising topically administering to said mammal a formulation of the present invention.

Discussion of Formulation Subembodiments

The invention can further be understood with reference to various subembodiments which can modify any of the principal embodiments. These subembodiments can be combined in any manner that is both mathematically and physically possible to create additional subembodiments, which in turn can modify any of the principal embodiments.

Suitable dosage forms for the formulations of this invention include gels, lotions, ointments, pastes and creams. The weight concentration of the chloroprocaine in the formulation will typically range from 1% to 5%, or from 2% to 4%, but most often will be approximately 3%. The chloroprocaine will typically be present as a salt, and this concentration will typically be based on the weight of the entire salt, although these percentages could also be used based on the weight of the free base. A particularly preferred salt for the formulations of the present invention is the hydrochloride salt.

The thickening agent is also an important component of the formulation for ensuring the stability of the formulation and its utility in medical applications, particularly ophthalmic applications. The thickening agent preferably yields a clear formulation, yet is easily processed to produce a product with appropriate viscosity and handling characteristics. Suitable thickening agents include, for example, cellulose derivatives, natural gums, and inorganic compounds. More particular examples include methyl cellulose, hydroxyethyl cellulose, hydroxypropyl cellulose, xanthan gum, guar gum, pectin, aluminum silicate, magnesium aluminum silicate, silica, and combinations thereof.

Hydroxyethyl cellulose has proven especially useful in the formulations of the present invention, at weight concentrations ranging from 0.1% to 2.5%. A preferred weight concentration of hydroxyethyl cellulose ranges from 0.25% to 2.0% by weight hydroxyethyl cellulose, or from 0.75% to 1.75%, with 1.0%, or 1.5% most preferred.

The formulations also benefit from the addition of a pH adjusting agent to prevent hydrolysis of the chloroprocaine. The pH of the formulations will preferably be reduced to a pH of from 1 to 6, from 2 to 5, or from 3 to 4 by the pH adjusting agent. Suitable pH adjusting agents for use in the formulations include hydrochloric acid, lactic acid, citric acid and tartaric acid, with hydrochloric acid most preferred. In concentration terms, hydrochloric acid equivalent to from 0.05% to 0.35% or from 0.10% to 0.25% 1N hydrochloric acid is typically added to the formulations, preferably from 0.13% to 0.17% 1N hydrochloric acid.

The formulations are aqueous-based formulations. The water used in the formulations is preferably purified and degassed through nitrogen bubbling or other suitable technique.

In any of the embodiments of the present invention, including the particular embodiments described in the immediately succeeding paragraphs:

the concentration of chloroprocaine HCl in the formulation can be 2-4 wt %, 2.5-3.5 wt %, or about 3.0 wt %;

the viscosity of the formulation can be 300-1500 mPas, 600-1400 mPas. 500-900 mPas, 600-750 mPas, 900-1500 mPas, or 1100-1400 mPas. I.e., hydroxyethyl cellulose can be added in an amount (q.s.) needed to achieve any of the foregoing viscosities;

the concentration of hydroxyethyl cellulose in the formulation can be 0.25-2.0 wt %, 0.5-1.5 wt %, 0.6-1.4 wt %, 0.5-1.0 wt %, 0.6-0.9 wt %, 0.7-0.8 wt %, 0.8-1.2 wt %, or 0.9-1.1 wt %; and/or the pH of the formulation can be 2.5-4.5 pH, 2.8-3.8 pH, or 3.0-3.4 pH. I.e., HCl can be added in an amount (q.s.) needed to achieve any of the foregoing pH levels.

In one particular embodiment, the formulation of the present invention comprises from 2% to 4% by weight chloroprocaine HCl; from 0.25 to 2.0% hydroxyethyl cellulose; hydrochloric acid q.s. to pH from 2.8 to 4.0 and purified water q.s. to 100%.

In another particular embodiment, the formulation of the present invention comprises from 2% to 4% by weight chloroprocaine HCl; from 0.6 to 0.9% hydroxyethyl cellulose; hydrochloric acid q.s. to pH from 2.8-4.0; and purified water q.s. to 100%.

In another particular embodiment, the formulation of the present invention comprises from 2% to 4% by weight chloroprocaine HCl; from 0.8 to 1.2% hydroxyethyl cellulose; hydrochloric acid q.s. to pH from 2.8-4.0; and purified water q.s. to 100%.

In another particular embodiment, the formulation of the present invention comprises from 2% to 4% by weight chloroprocaine HCl; hydroxyethyl cellulose q.s. to 600-1400 mPas; hydrochloric acid q.s. to pH from 2.8 to 4.0; and purified water q.s. to 100%.

In another particular embodiment, the formulation of the present invention comprises from 2% to 4% by weight chloroprocaine HCl; hydroxyethyl cellulose q.s. to 500-900 mPas; hydrochloric acid q.s. to pH from 2.8 to 4.0; and purified water q.s. to 100%.

In another particular embodiment, the formulation of the present invention comprises from 2% to 4% by weight chloroprocaine HCl; hydroxyethyl cellulose q.s. to 600-800 mPas; hydrochloric acid q.s. to pH from 3.0 to 3.4; and purified water q.s. to 100%.

In another particular embodiment, the formulation of the present invention comprises from 2% to 4% by weight chloroprocaine HCl; hydroxyethyl cellulose q.s. to 900-1500 mPas; hydrochloric acid q.s. to pH from 2.8 to 4.0; and purified water q.s. to 100%.

In another particular embodiment, the formulation of the present invention comprises from 2% to 4% by weight chloroprocaine HCl; hydroxyethyl cellulose q.s. to 1100-1400 mPas; hydrochloric acid q.s. to pH from 3.0 to 3.4; and purified water q.s. to 100%.

In a particularly preferred embodiment the formulation of the present invention comprises 3% by weight chloroprocaine HCl; from 0.25 to 2.0% hydroxyethyl cellulose; hydrochloric acid in a volume equivalent to 0.17% to 0.13% 1N hydrochloric acid; and purified water q.s. to 100%.

The formulations can also be characterized by other features. For example, in any of the embodiments of this invention the formulation is preferably sterile. In addition, in any of the embodiments the formulation preferably has a viscosity of from 100 to 12000 mPas or from 1000 to 10000 mPas, or from 4000 to 9000 mPas, as measured by a BrookField DV II+Pro 2 or 3 speed Spindle at 100 rpm, as described in section 2.2.10 of the European Pharmacopeia 2016 edition. The formulation also is preferably either clear or translucent.

Methods of Treatment

The formulations of the present invention can be used in any method that topical anesthetics have historically been used, although they have particular utility in ophthalmic applications. The formulations have been found effective for inducing local anesthesia or analgesia on the corneal surface, and can be used during ocular surgery or in response to a corneal abrasion or trauma. Particularly suitable surgeries for practicing the present invention include, for example, cataract surgery, treatment for maculopathy, conventional glaucoma surgery, vitrectomy, surgeries for diabetic nephropathy, and various laser surgeries including laser-assisted in situ keratomileusis and photorefractive keratectomy.

The formulations induce local analgesia or anesthesia in the eye, and they do so without inducing significant irritation.

Methods of Manufacture

The formulations of the present invention can be manufactured using conventional manufacturing techniques as described, for example, in REMINGTON: THE SCIENCE AND PRACTICE OF PHARMACY (22d edition), although several discoveries have been made to improve their manufacture.

For example, it has been discovered the the formulations can be handled in the presence of air, without nitrogen purge. Thus, for example, the finished formulation can be filled into suitable containers such as sachets, tubes, jars and vials, in the presence of air.

While the drug product can be packaged in various packaging formats, a preferred packaging format is a monodose presentation that contains approximately 0.5 to 2 grams of gel. For example, the drug can be packaged in a small envelope of opposing sheets sealed around their periphery that is torn at one end before use, and the gel squeezed from the container. A preferred package is a low density polyethylene monodose vial such as the 1840 H LDPE from LyondellBasell Industries N.V., Rotterdam Netherlands.

In addition, the inventors have developed a sterilization process for the drug solution, prior to mixing with the gel excipients. This is achieved using filtration sterilization for the drug solution through a hydrophilic cartridge having a pore width of from 0.22 to 0.45 microns.

In one subembodiment, which is particularly suitable for making higher viscosity formulations, the process of admixing all of the formulation ingredients is divided into several discreet steps comprising (a) admixing said one or more thickening agents, said pH adjuster, and water to make a placebo matrix, (b) thermally sterilizing the placebo matrix, (c) admixing chloroprocaine or a pharmaceutically acceptable salt thereof with water and optionally a pH adjuster to prepare a drug solution, (d) sterilizing said drug solution by filtering said drug solution through a filter having a pore width of from 0.22 to 0.45 microns, and (e) mixing the placebo matrix and the drug solution to make said formulation.

In this subembodiment one or all of the following conditions can be observed:
- the chloroprocaine can be dissolved in water at about 40° C. to a concentration of 0.06-0.1 g/mL to ensure the chloroprocaine is fully solubilized without precipitation.
- the chloroprocaine/water solution can be acidified with HCl at about 40° C. so that the stability or solubility of the chloroprocaine is unaffected; thus not affecting neither API degradation nor its solubility.
- the placebo matrix can be allowed to cool prior to the addition of the drug solution.
- the chloroprocaine/water solution can be transferred via sterilizing filtration towards the hydroxyethyl cellulose solution/placebo matrix.
- the residuals in the vessel used to mix the chloroprocaine and water can be washed with around 5% of the water and added back to the chloroprocaine/hydroxyethyl cellulose mixture.

Regardless of the manufacturing method, hydroxyethyl cellulose is the preferred thickening agent, in an amount which imparts the desired viscosity, and hydrochloric acid (1N) is the preferred pH adjusting agent, the process preferably comprises admixing 3% by weight chloroprocaine HCl, 0.25 to 2.0% hydroxyethyl cellulose, hydrochloric acid q.s. to pH 3.0-4.0 (or in a volume equivalent to 0.17% to 0.13% 1N hydrochloric acid) and purified water q.s. to 100% to make the formulation.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1. Manufacture of Formulations

Using the raw materials described in Table 1a, 3% chloroprocaine gels having the formulations in Tables 1b and 1c were manufactured as follows:

TABLE 1a

| Raw Material Listing | |
| --- | --- |
| Raw material-trade name | Phase |
| Purified Water | A |
| Hydroxy ethylcellulose (Natrosol 250M Pharma ™) | B |

TABLE 1a-continued

| Raw Material Listing | |
| --- | --- |
| Raw material-trade name | Phase |
| Chloroprocaine Hydrochloride | C |
| Hydrochloric Acid 1N | D |

In a suitable mixing machine equipped with a stirrer and homogenizer, B was added in small portions to A under stirring until a homogeneous gel formed without undispersed particles. If necessary, the mixture can be heated up to 60° C. The mixture was then cooled under stirring until it reached a temperature of 25-28° C. C was then added and stirred until complete formation of a homogenous gel without undispersed particles. The pH was then adjusted to 2.70-4.00 by the addition of D, and the mixture was sterilized through a sterile filter having a pore size of from 0.22 to 0.45 microns.

TABLE 1b

| Formulation 1 | | |
| --- | --- | --- |
| Raw materials | Purpose | % |
| Purified Water | Solvent | 96.330 |
| Hydroxy ethylcellulose | Thickening agent | 0.500 |
| Chloroprocaine Hydrochloride | Active Pharmaceutical Ingredients | 3.000 |
| Hydrochloric Acid 1N | pH modifier | 0.170 |
| Total | | 100.000 |

TABLE 1c

| Formulation 2 | | |
| --- | --- | --- |
| Raw materials | Purpose | % |
| Purified Water | Solvent | 95.850 |
| Hydroxy ethylcellulose | Thickening agent | 1.000 |
| Chloroprocaine Hydrochloride | Active Pharmaceutical Ingredients | 3.000 |
| Hydrochloric Acid 1N | pH modifier | 0.150 |
| Total | | 100.000 |

A similar formulation could be prepared, using an even higher concentration of hydroxyethyl cellulose (such as 1.5%), using substantially the same proportions of excipients as formulations 1 and 2, and the methods described herein.

Example 2. Alternative Manufacturing Method and Formulations

Using the raw materials substantially as described in Table 1a, 3% chloroprocaine gels having the formulations in Table 2b were manufactured according to the process flow chart given in Table 2a:

TABLE 2a

| Process flow chart: | | | |
| --- | --- | --- | --- |
| API phase | Gel phase | In-process controls API phase | In-process controls Gel phase |
| Addition of about 40% of water for injection | Addition of about 40% of water for injection | | |

TABLE 2a-continued

Process flow chart:

| API phase | Gel phase | In-process controls API phase | In-process controls Gel phase |
|---|---|---|---|
| Cooling at 40° C. Addition of Chloroprocaine and stirring up to complete dissolution pH adjustment at 3.0 with HCl 1N Sterilizing filtration | Cooling at 40° C. Addition of hydroxyethyl cellulose and stirring up to complete dissolution Sterilization by heat ($F_0$) | Aspect, pH, bioburden Integrity test on filter | Aspect, viscosity, bioburden |
| Transfer ⟶ | | | In-process controls |
| | Completion with missing water quantity Clarification filtration (45 micron) Filling Secondary packaging | | pH, viscosity Fill weight Leak test |

TABLE 2b

Formulations

| | Trial number | | | | | |
|---|---|---|---|---|---|---|
| Components | E08 | E09 | E10 | E11 | E12 | E13 |
| | Proportions (m/m) % | | | | | |
| Chloroprocaïne HCL | 3.0 | 3.0 | 3.0 | 3.0 | 3.0 | 3.0 |
| Natrosol * | 1.0 | 0.75 | 1.5 | 1.25 | 1.0 | 1.15 |
| Purified water (gel phase) | 41.0 | 41.0 | 41.0 | 41.0 | 41.0 | 41.0 |
| Purified water (API phase) | 50.0 | 50.0 | 50.0 | 50.0 | 50.0 | 50.0 |
| Purified water (washing) | ~5.0 | ~5.0 | ~4.5 | ~4.75 | ~5.0 | ~5.0 |
| HCl (1N or 10%) | Up to pH 3.0-4.0 | | | | | |

* H or HHX grade depending on the targeted viscosity (H for E08, HHX for other trials)

Viscosity of the formulations described in Table 2B was measured by a BrookField DV II+Pro 2 or 3 speed Spindle at 100 rpm, as described in section 2.2.10 of the European Pharmacopeia 2016 edition. Results of viscosity measurements are reported in Table 3c.

TABLE 3c

Viscosity Measurements

| | E08 | E09 | E10 | E11 | E12 | E13 |
|---|---|---|---|---|---|---|
| Viscosity (mPas) | 660 | 660 | More than 3500 | 2320 | 1308 | 1577 |
| Industrial feasibility | Yes | Yes | Not likely | Not likely | Yes | Yes likely |

Example 3. Formulation Stability Studies

The formulations described in Tables 1b and 1c were tested for stability after six months of storage at 20° C.±5° C. protected from light in two types of packaging: glass packs and glass vials with butyl set and aluminum crimp sealer. Methods for performing the stability analyses are described in Table 3a. The results of the stability testing are reported in Table 3b.

TABLE 3a

Test Items and Analytical Procedures

| Test Item | Analytical Procedure |
|---|---|
| Appearance | visual |
| pH (as is) | pH metro: MetrOhm 744 (Rif DM12); Ref. Ph Eur 2.2.3 current edition |
| Viscosity (mPas) | BrookField DV II + Pro Spindle, 100 rpm Ref. Ph Eur 2.2.10 current edition* |
| Chloroprocaine HCl Assay % | HPLC |
| Impurity ACBA % (HPLC) | HPLC |
| Impurity Hydroxyprocaine % (HPLC) | HPLC |
| Unknown impurity | HPLC |
| Total impurities % (known + unknown) (HPLC) | HPLC |

*A 2-speed spindle was employed for the 90 mPas formula 1; a 3-speed spindle was employed for the 400 mPas formula 2.

TABLE 3b

Formulation 1 Stability

| Test | $T_0$ | $T_{6mo}$ (before sterilization) | $T_{6mo}$ (after sterilization) |
|---|---|---|---|
| Appearance | passes | passes | passes |
| pH | 3.6 | 3.2 | not checked |
| chloroprocaine HCl (%) | 105.48 | 103.88 | 104.10 |
| total impurities (%) | 0.402 | 0.679 | 0.653 |

TABLE 3c

Formulation 2 Stability

| Test | $T_0$ | $T_{6mo}$ (before sterilization) | $T_{6mo}$ (after sterilization) |
|---|---|---|---|
| Appearance | passes | passes | passes |
| pH | 3.39 | 3.21 | not checked |
| chloroprocaine HCl (%) | 107.18 | 111.47 | 105.72 |
| total impurities (%) | 0.408 | 0.727 | 0.662 |

Example 3. Efficacy Study in Rabbits

The anesthetic effect of chloroprocaine HCl formulations following a single instillation in albino rabbits was evaluated using the below-described protocol. Eighteen animals were included in this study and divided into 6 groups of three animals each. The test formulations, negative control formulation and positive control were instilled (50 µL per administration) in the right eyes on Days 1 and 5, in the left eyes on Day 2. The formulations tested are described in Table 3a.

TABLE 3a

Test Formulations

| Group No. | Treatment | Animal Nos. |
|---|---|---|
| 1 | 3% Chloroprocaine HCl Gel (Formulation 1) | 1, 2, 3 |
| 2 | 3% Chloroprocaine HCl Gel (Formulation 2) | 4, 5, 6 |
| 3 | 5% Chloroprocaine Gel | 7, 8, 9 |
| 4 | 3% Chloroprocaine HCl Liquid | 10, 11, 12 |
| 5 | Negative control (NaCl 0.9%) | 13, 14, 15 |
| 6 | Positive control Cebesine ® (0.4% Oxybuprocaine HCl solution) | 16, 17, 18 |

The study was organized into two stages: Stage 1 determined the smallest stimulus (i.e. threshold length of nylon thread) necessary to induce a blinking reflex in the animals after instillation of each of the treatments. Several lengths of nylon were tested to determine the shortest length. This stage gave an idea of the intensity of anesthetic power of each compound at 5 and 15 minutes, and identified a single thread length (2.1 cm) for use in the next stage.

Stage 2 evaluated the duration of anesthesia using the selected threshold. All treatments were evaluated except animals treated with test item 3, due to intolerance observed with the 5% dose. The duration of anesthesia for each group was tested with the same length of nylon thread determined in stage 1, so that the mechanical stimulus intensity was the same for all groups. This stage evaluated the start of effect and duration of effect at a given level of mechanical stimulus.

Formulations 1 and 2 were well tolerated in spite of their low pH. In stage 1, formulations 1 and 2 were the most efficient test items (comparable to positive control) in terms of depth of anesthesia followed by formulation 4. In stage 2, an anesthesia effect was observed, from 5 minutes after the instillation, until 45 minutes for formulation 1, 60 minutes for formulation 2, 20 minutes for formulation 4, and 90 minutes for Cebesine®. No anesthetic effect was observed for the negative control. Based on these tests, an even more viscous formulation with a longer duration of action, using for example 1.5% or 2% hydroxyethyl cellulose, could also be used.

Other Embodiments

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A topical ophthalmic gel formulation comprising from 2% to 4% by weight of chloroprocaine or a pharmaceutically acceptable salt thereof, one or more thickening agents, and water, at a pH of from 2.8 to 3.8.

2. The formulation of claim 1 comprising from 2% to 4% by weight chloroprocaine HCl.

3. The formulation of claim 1 comprising about 3% by weight chloroprocaine HCl.

4. The formulation of claim 1 comprising from 0.5% to 1.5% by weight hydroxyethyl cellulose.

5. The formulation of claim 1 at a pH of from 3.0 to 3.6.

6. The formulation of claim 1 further comprising hydrochloric acid.

7. The formulation of claim 1 comprising hydroxyethyl cellulose in an amount sufficient to impart a viscosity of from 300 to 4000 mPas.

8. The formulation of claim 1 in the form of a monodose container comprising from 0.5 to 2 grams of gel.

9. The formulation of claim 1 comprising about 3% by weight chloroprocaine HCl, hydrochloric acid, and from 0.5% to 1.5% by weight hydroxyethyl cellulose.

* * * * *